United States Patent [19]

Yanai et al.

[11] Patent Number: 4,460,597
[45] Date of Patent: Jul. 17, 1984

[54] HERBICIDAL 5-AMINOALKOXY-4-BENZOYL-1,3-DIMETHYL-PYRAZOLE DERIVATIVES

[75] Inventors: Toshiaki Yanai; Teruomi Jojima, both of Hiromachi; Katsuhiko Kawakubo, Shiga; Toyokuni Honma, Shiga; Masahiro Shindo, Shiga, all of Japan

[73] Assignee: Sankyo Company, Limited, Tokyo, Japan

[21] Appl. No.: 496,815

[22] Filed: May 23, 1983

[30] Foreign Application Priority Data

May 25, 1982 [JP] Japan .................................. 57-88542

[51] Int. Cl.³ .................... A01N 43/56; C07D 231/20
[52] U.S. Cl. ............................... 424/273 P; 548/377; 548/378
[58] Field of Search .............................. 548/377, 378; 424/273 P

[56] References Cited

U.S. PATENT DOCUMENTS 4,266,963 5/1981 Nishiyama et al. ................. 548/377

OTHER PUBLICATIONS

The Morrison and Boyd Textbook of Organic Chemistry, 1978, p. 734.

Primary Examiner—Henry R. Jiles
Assistant Examiner—J. G. Mullins
Attorney, Agent, or Firm—Frishauf, Holtz, Goodman & Woodward

[57] ABSTRACT

Pyrazole derivatives of formula (I):

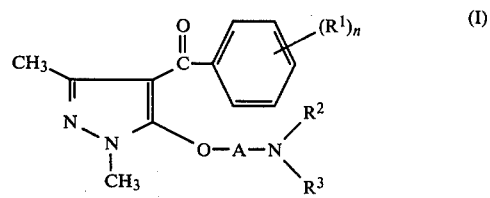

($R^1$ is methyl, halogen or nitro; n is 2 or 3; $R^2$ is hydrogen, $C_{1-4}$ alkyl, $C_{3-4}$ alkenyl or aralkyl; $R^3$ is $C_{1-4}$ alkyl, $C_{3-4}$ alkenyl or phenyl; A is $C_{1-5}$ alkylene) are of use as herbicides.

6 Claims, No Drawings

HERBICIDAL 5-AMINOALKOXY-4-BENZOYL-1,3-DIMETHYL-PYRAZOLE DERIVATIVES

BACKGROUND OF THE INVENTION

This invention relates to novel pyrazole derivatives and their use as herbicides. The invention provides the pyrazole derivatives themselves, processes for their preparation, compositions containing them, and methods for their use.

Japanese Patent Application Laid Open No. 126830/1975 discloses pyrazole derivatives having the formula below and their use as herbicides:

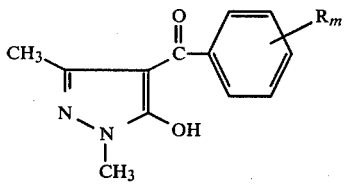

(wherein R represents a halogen atom, a nitro group or lower alkyl group and m is 1, 2, 3 or 4, the groups R being the same or different when m is 2, 3, or 4). The Japanese text also discloses salts and esters of these compounds.

OBJECT OF THE INVENTION

It is the object of this invention to provide new pyrazole derivatives of use as herbicides.

SUMMARY OF THE INVENTION

The present inventors have found a different class of pyrazole derivatives which possess good herbicidal activity. The pyrazole derivatives of this invention have the formula (I):

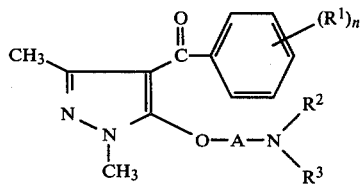

wherein:
$R^1$ is selected from the group consisting of a methyl group, a halogen atom and a nitro group;
n is 2 or 3;
$R^2$ is selected from the group consisting of a hydrogen atom, an alkyl group having 1 to 4 carbon atoms, an alkenyl group having 3 or 4 carbon atoms and an aralkyl group having 1 or 2 carbon atoms in the alkyl portion and optionally substituted on the aryl portion;
$R^3$ is selected from the group consisting of an alkyl group having 1 to 4 carbon atoms, an alkenyl group having 3 or 4 carbon atoms and a phenyl group; and
A is an alkylene group having from 1 to 5 carbon atoms.

PREFERRED EMBODIMENTS

The lower alkyl groups $R^2$ and $R^3$ may be straight or branched alkyl groups having from 1 to 4 carbon atoms, such as methyl, ethyl, n-propyl, i-propyl, n-butyl, i-butyl or tert-butyl groups, and are preferably methyl or ethyl groups.

Where $R^2$ or $R^3$ represents an alkenyl group, it may be a straight or branched chain alkenyl group having 3 or 4 carbon atoms such as an allyl, methallyl or 2-butenyl group, preferably an allyl group. Where $R^2$ is an aralkyl group, it may be a benzyl or phenethyl group, and is optionally substituted on the aryl portion with, for example, an alkyl group having 1 to 4 carbon atoms, such as a methyl group.

The alkylene group A may be a straight or branched alkylene group having from 1 to 5 carbon atoms, such as a methylene, ethylene, methylmethylene, trimethylene, ethylmethylene, dimethylmethylene, propylene, tetramethylene, 1,1-, 1,2- or 2,2-dimethylethylene, 1- or 2-ethylethylene or pentamethylene group, and is preferably an ethylene or trimethylene group.

A preferred group of compounds within the above formula (I) of this invention are those wherein A represents an ethylene group; $R^2$ represents a hydrogen atom, a methyl group, an ethyl group an allyl group or a benzyl group; $R^3$ represents a methyl group, an ethyl group or a phenyl group. Particularly preferred are compounds wherein $(R^1)_n$ represents a 2,4-dichloro substituent.

SPECIFIC COMPOUNDS OF THE INVENTION

Specific examples of compounds (I) of this invention are given by way of illustration in the following list. The compound numbers are used elsewhere in this specification.

| No | $R^1$ | A | $R^2$ | $R^3$ |
|---|---|---|---|---|
| 1 | 2,4-$Cl_2$ | —$(CH_2)_2$— | H | phenyl |
| 2 | 2,4-$Cl_2$ | —$(CH_2)_2$— | $CH_3$ | phenyl |
| 3 | 2,4-$Cl_2$ | —$(CH_2)_3$— | $CH_3$ | phenyl |
| 4 | 2,4-$Cl_2$ | —$(CH_2)_4$— | $CH_3$ | phenyl |
| 5 | 2,4-$Cl_2$ | —$CH_2$—$\underset{CH_3}{\overset{CH_3}{C}}$—$CH_2$— | $CH_3$ | phenyl |
| 6 | 2,4-$Cl_2$ | —$CH(CH_3)$—$CH_2$— | $CH_3$ | phenyl |
| 7 | 2,4-$Cl_2$ | —$(CH_2)_2$— | $C_2H_5$ | $C_2H_5$ |
| 8 | 2,4-$Cl_2$ | —$(CH_2)_3$— | H | phenyl |
| 9 | 2,4-$Cl_2$ | —$(CH_2)_2$— | i-$C_3H_7$ | phenyl |
| 10 | 2,4-$Cl_2$ | —$(CH_2)_2$— | n-$C_4H_9$ | phenyl |
| 11 | 2,4-$Cl_2$—3-$CH_3$ | —$(CH_2)_2$— | $CH_3$ | phenyl |
| 12 | 2,4-$Cl_2$ | —$(CH_2)_2$— | $C_2H_5$ | phenyl |
| 13 | 2,4-$Cl_2$ | —$(CH_2)_2$— | allyl | phenyl |
| 14 | 2,4-$Cl_2$ | —$(CH_2)_2$— | benzyl | phenyl |
| 15 | 2,4-$Cl_2$ | —$(CH_2)_2$— | benzyl | $CH_3$ |
| 16 | 2-$NO_2$—4-Cl | —$(CH_2)_2$— | allyl | $C_4H_9$ (n) |
| 17 | 2-$NO_2$—4-Cl | —$(CH_2)_2$— | $CH_3$ | phenyl |
| 18 | 2-$NO_2$—5-$CH_3$ | —$(CH_2)_2$— | $CH_3$ | phenyl |
| 19 | 2-$NO_2$—3,5-$(CH_3)_2$ | —$(CH_2)_2$— | allyl | phenyl |
| 20 | 2,4-$Cl_2$—3-$CH_3$ | —$(CH_2)_2$— | allyl | allyl |

PREPARATIVE PROCESSES

The present invention also provides processes for preparing the compounds of formula (I) of this invention.

Process (A-1)

The compounds of formula (I) can be prepared by reacting a compound of formula (II):

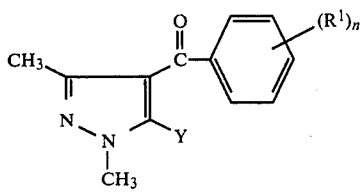

(wherein $R^1$ and n are as defined above and Y is a halogen atom) with a compound of formula (III):

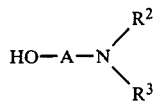

(wherein $R^2$, $R^3$ and A are as defined above).

In reacting the 5-halopyrazole derivative (II) with the aminoalcohol (III), it is possible to proceed in various ways. For example, the reaction can be effected by (a) first preparing an alkali metal alkoxide of the aminoalcohol (III), and then reacting this alkoxide with derivative (II), or (b) reacting the aminoalcohol (III) with the derivative (II) in the presence of an organic base, or (c) reacting derivative (II) with an excess of the aminoalcohol. Other ways of effecting the reaction can be used.

In general, the reaction (A-1) can be carried out in the absence or presence of a solvent. The nature of any solvent which is employed is not critical, as long as the solvent does not participate in the reaction. For instance, the solvent can be selected from aromatic hydrocarbons such as benzene or toluene; amides such as dimethylformamide or dimethylacetamide; ethers such as tetrahydrofuran or dioxan; or mixtures thereof. The reaction is preferably carried out in the absence of a solvent or in the presence of a mixed solvent which is a mixture of aromatic hydrocarbon and aprotic polar solvent.

The reaction is preferably effected in the presence of a base, which may be an alkoxide formed from the aminoalcohol by reaction with an appropriate separate base, as in (a) above, or be a separate base, as in (b) above, or be an excess of the aminoalcohol itself, as in (c) above. For the separate base, there may be mentioned, for instance, alkali metals such as potassium or sodium; alkali metal hydrides such as sodium hydride or potassium hydride; and organic bases such as pyridine or triethylamine. The reaction can be carried out by the use of the theoretical amount of aminoalcohol, but in order to accomplish the reaction more speedily, usually the use of an excess amount (about 2 to 10 mols of (III) per mol (II) is preferable. The reaction can be effected for example at from room temperature to 150° C., and generally is finished within 15 hours. After completion of the reaction, the desired product can be recovered from the reaction mixture by means of conventional techniques. For instance, the solvent and the excess aminoalcohol can be distilled off under reduced pressure, and the desired product obtained for instance by distillation of the residue under reduced pressure or by purification using column chromatography.

Process (A-2) In another process of this invention, a pyrazole derivative having the formula (Ia) is prepared;

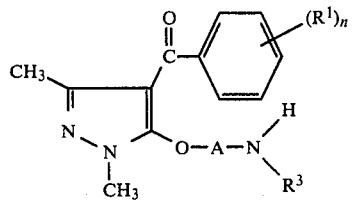

(wherein $R^1$, n, $R^3$, and A are as defined above) by reacting a compound of formula (II):

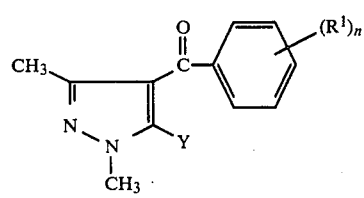

ps (wherein $R^1$, n and Y are as defined above) with a compound of formula (IV):

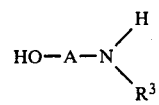

(wherein $R^3$ and A are as defined above).

In turn, such a compound of formula (Ia), whether or not prepared from a compound (II), can be used to prepare a compound of formula (Ib):

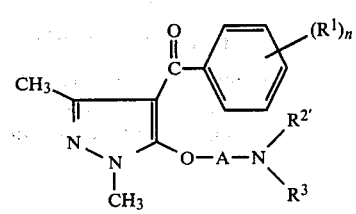

(wherein $R^1$, $R^3$, n and A are as defined above and $R^{2'}$ is selected from the group consisting of an alkyl group having 1 to 4 carbon atoms, an alkenyl group having 3 or 4 carbon atoms and an aralkyl group having 1 or 2 carbon atoms in the alkyl portion and optionally substituted on the aryl portion) by reaction with a compound of formula (V):

$$R^{2'}-Y \qquad (V)$$

(wherein $R^{2'}$ and Y are as defined above).

In these processes, the reaction conditions to produce the compound (I-a) can be the same as for the process (A-1). To produce the compound (I-b), the compound (I-a) is reacted with a halide compound (V), usually in a solvent. As examples of the solvent which may be employed, there may be mentioned aromatic hydrocarbons such as benzene or toluene; dimethylformamide; dimethyl sulphoxide; ethers such as tetrahydrofuran or dioxan; alcohols such as methanol, ethanol or propanol; halogenated hydrocarbons such as chloroform or carbon tetrachloride; ketones such as methyl ethyl ketone or i-butyl methyl ketone; nitriles such as acetonitrile; or water. The reaction to produce compound (Ib) is best effected in the presence of a base. Examples of appropriate bases include alkali metal hydroxides such as sodium hydroxide or potassium hydroxide; alkali metal carbonates such as sodium carbonate or potassium carbonate; or organic bases such as pyridine or triethylamine.

Process (B)

The compounds of formula (I) can also be prepared by reacting a compound of formula (VI):

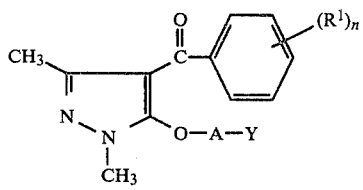

(wherein $R^1$, n, A and Y are as defined above) with a compound of formula (XI):

(wherein $R^2$ and $R^3$ are as defined above). The reaction is best effected in the presence of an acid binding agent.

The above reaction can be carried out in the absence or presence of a solvent. Suitable solvents comprise those which do not participate in the reaction: for example, there may be mentioned ethers such as tetrahydrofuran or dioxan; aromatic hydrocarbons such as benzene, toluene or xylene; halogenated hydrocarbons such as chloroform or carbon tetrachloride; ketones such as methyl ethyl ketone or i-butyl methyl ketone; esters such as ethyl acetate or amyl acetate; nitriles such as acetonitrile; or mixtures thereof. It is preferred to use an aromatic hydrocarbon.

As for the acid binding agent, there may be mentioned, for instance, organic bases such as pyridine, triethylamine or N,N-diethylaniline; or the amine (XI) if used in excess. The reaction temperature is not particularly critical, and may be from the reflux temperature of any solvent employed to 150° C. The duration of the reaction is normally from 1 to 15 hours. After completion of the reaction, the desired product can be isolated by conventional techniques, and, if desired, purified by conventional procedures such as distillation under reduced pressure or using column chromatography.

The compounds of formula (VI) can prepared by reacting a compound of formula (VII):

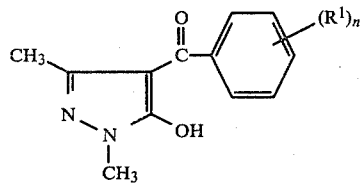

(wherein $R^1$ and n are as defined above) with a dihalide (VIII):

(wherein A and Y are as defined above) in the presence of an acid binding agent.

The reaction is generally carried out in the presence of a solvent. For the solvent, there may be mentioned, for instance, nitriles such as acetonitrile or propionitrile; dimethylformamide; or dimethyl sulphoxide. The acid binding agent can be one of those given for the process (A-2). In particular, it is preferred to use an alkali metal hydroxide such as sodium hydroxide or potassium hydroxide.

Process (C)

The compounds of formula (I) can also be prepared by reacting a compound of formula (IX):

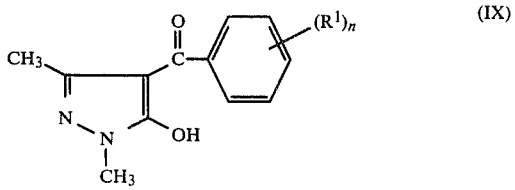

(wherein $R^1$ and n are as defined above) with a compound of formula (X):

(wherein $R^2$, $R^3$ A and Y are as defined above). This reaction is best effected in the presence of an acid binding agent.

The reaction can be carried out in the absence or presence of a solvent. The solvent is suitably any solvent which does not participate in the reaction, and there may be mentioned, for instance, nitriles such as acetonitrile or propionitrile; ethers such as tetrahydrofuran or dioxan; halogenated hydrocarbons such as chloroform or dichloroethane; ketones such as methyl ethyl ketone or i-butyl ketone; dimethylformamide or dimethyl sulfoxide. More particularly, it is preferred to use a nitrile as solvent.

The reaction is preferably carried out in the presence of an acid binding agent. The acid binding agent can be one of the agents described for the process (A-2). The reaction temperature is not particularly critical and may be from room temperature to the reflux temperature of the solvent. The duration of the reaction is typically from 1 to 15 hours.

HERBICIDAL ACTIVITY

The compounds of the above-mentioned formula (I) are of use as herbicides and kill weeds by inducing a strong chlorosis.

In paddy fields, a particularly potent herbicidal effect can be obtained against perennial weeds by pre- and post-emergence treatment in soil, without any harmful effect on newly-transplanted rice plants and growing rice plants. Examples of perennial weeds which can be combatted include those of the family Cyperaceae, for example, "Hotarui" (*Scirpus hotarui Ohwi*), flatsedge (*Cyperus serotinus Rottb.*) and the like and those of the family Alismataceae, for example, arrowhead (Omodaka) (*Sagittaria trifolia L.*) and arrowhead (Urikawa) (*Sagittaria pygmea Miq.*). Such weeds are difficult to control with conventional herbicides. Furthermore, monocotyledonous weeds can be controlled, such as those of the family Gramineae, for example, barnyard grass and panic grass, and broad leaved weeds such as those of the family Scrophulariaceae, for example, false pimpernel, "Murasakisagigoke" (*Mazus miquelii Makino*) and "Abunome" (*Dopatrium junceum Hamilt*), weeds of the family Cruciferae, for example wavy bittercress, marsh yellow cress and "Mizutagarashi" (*Cardamine lyrate Bunge*), weeds of the family Lythraceae, for example toothcup and "Mizumatsuba" (*Rotala mexicana Cham.*), and weeds of the family Compositae, for example, ragwort and American false daisy.

In upland fields, pre- and post-emergence treatment with compounds (I) of this invention in soil can show particularly potent effect against weeds of the family Caryophyllaceae, for example, common chickweed, bog stichwort, mouse-ear chickweed and pearlwort and, furthermore, effective control can be obtained of weeds of the family Portulacaceae, for example, common purslane, weeds of the family Amaranthaceae, for example, rough pigweed, weeds of the family Chenopodiaceae, for example, "Akaza" (*Chenopodium album L.*), common lamb's quarters and "Koakaza" (*Chenopodium ficifolium Smith*), weeds of the family Commelinaceae, for example, Asiatic dayflower, weeds of the family Labiatae, for example, henbit, "Kiranso" (*Ajuga decumbens Thunb.*), weeds of the family Oxalidaceae, for example, creeping wood sorrel and violet wood sorrel, weeds of the family Leguminosae, for example, "Nekonagi" (*Lespedeza pilosa Sieb et Zucc.*), hairy vetch and common vetch, and weeds of the family Euphoribiaceae, for example, Virginia copperleaf and milk purslane.

Narrow leaved weeds, in particular, those of the family Cyperaceae, such as "Kayatsurigusa" (*Cyperus mictroiria Steud.*) can be effectively controlled and those of the family Gramineae such as wheatgrass and crab-grass, "Komehishiba" (*Digitaria timorensis Balansa*), "Akinoenokorogusa" (*Setaria faberi Herrmann*), and foxtail can also be effectively controlled. On the other hand, crops such as rice plants, cereals, sugar beets, soybeans, cotton plants, radishes, tomatoes, carrots, Chinese cabbages and lettuces do not suffer from phytotoxicity on exposure to herbicidally effective amounts of compounds (I) of this invention.

Additionally, the compounds of the formula (I) are effective as herbicides in other applications, for example in fruit gardens, unplanted fields or forests.

If desired, the compounds of this invention may be used as their salts formed with suitable acids.

The compounds of this invention may be formulated for use in the manner of preparations commonly employed for herbicides, for example, as dusts, coarse dusts, fine granules, granules, wettable powders, emulsifiable concentrates, aqueous liquids, water-soluble preparations, oil suspensions and so on, with admixture of a carrier or diluent and if required, other auxiliary agents. Thus, the present invention further provides herbicidal compositions containing a carrier or diluent and an effective amount of a pyrazole derivative having the formula (I).

The carrier may usefully be a synthetic or natural, inorganic or organic substance that can assist the active compound to reach the portion to be treated, and make it easy to admix, store, transport, or handle the active compound in the herbicidal composition.

Suitable solid carriers include inorganic substances such as clays (which may be represented by kaolinite, montmorillonite or attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances such as soy-bean meal, tobacco powder, walnut powder, wheat flour, wood meal, starch and crystalline cellulose; synthetic or natural high polymer compounds such as cumarone resin, petroleum resin, alkyd resin, polyvinyl chloride, polyalkylene glycol, ketone resin, ester gum, copal gum and dammar gum; waxes such as carnauba wax or beeswax; or urea.

As suitable liquid carriers may be mentioned paraffin or naphthene hydrocarbons such as kerosine, mineral oil, spindle oil or white oil; aromatic hydrocarbons such as benzene, toluene, xylene, ethylbenzene, cumene or methylnaphthalene; chlorinated hydrocarbons such as carbon tetrachloride, chloroform, trichloroethylene, monochlorobenzene or o-chlorotoluene; ethers such as dioxan or tetrahydrofuran; ketones such as acetone, methyl ethyl ketone, diisobutyl ketone, cyclohexanone, acetophenone or isophorone; esters such as ethyl acetate, amyl acetate, ethylene glycol acetate, diethylene glycol acetate, dibutyl maleate or diethyl succinate; alcohols such as methanol, n-hexanol, ethylene glycol, diethylene glycol, cyclohexanol or benzyl alcohol; ether alcohols such as ethylene glycol ethyl ether, ethylene glycol phenyl ether, diethylene glycol ethyl ether or diethylene glycol butyl ether; polar aprotic solvents such as dimethylformamide or dimethyl sulfoxide; or water.

Surface active agents can usefully be included in the compositions of this invention, for example, for emulsification, dispersion, wetting, spreading, binding, controlled disintegration, stabilization of the active ingredient, improving fluidity or rust proofing. Any non-ionic, anionic, cationic or amphoteric surfactant may be used, but non-ionic and/or anionic agents are preferred. As suitable non-ionic surface active agents may be mentioned, for example, polymerization adducts of ethylene oxide to higher alcohols such as lauryl alcohol, stearyl alcohol or oleyl alcohol; polymerization adducts of ethylene oxide to alkyl phenols such as isooctyl phenol or nonyl phenol; polymerization adducts of ethylene oxide to alkyl naphthols such as butyl naphthol or octyl naphthol; polymerization adducts of ethylene oxide to higher fatty acids such as palmitic acid, stearic acid or oleic acid; polymerization adducts of ethylene oxide to mono- or di-alkyl phosphoric acids such as stearyl phosphoric acid or dilauryl phosphoric acid; polymerization adducts of ethylene oxide to amines such as dodecyl amine or stearic acid amide; polymerization adducts of ethylene oxide to higher fatty acid esters of polyhydric alcohols such as sorbitan or fatty acid esters; polymerization adducts of ethylene oxide to propylene oxide; and so on. As suitable anionic surface active agents may be mentioned, for example, alkyl sulphate salts such as sodium lauryl sulphate or oleyl sulphate amine salt; alkyl sulphonate salts such as sodium dioctyl sulphosuccinate or sodium 2-ethylhexene sulphonate; and aryl sulphonate salts such as sodium isopropylnaphthalene sulphonate, sodium methylenebisnaphthalene sulphonate, sodium ligninsulphonate or sodium dodecylbenzene sulphonate.

Moreover, the herbicidal compositions of this invention may be used in combination with high molecular compounds or other auxiliary agents such as casein, gelatin, albumin, glue, sodium alginate, carboxymethyl cellulose, methyl cellulose, hydroxyethyl cellulose or polyvinyl alcohol for improved properties and increased biological effectiveness thereof.

The carriers and various auxiliary agents may be used alone or in any desired combination depending on the type of preparation, the application and other factors.

Dusts may conveniently contain, for example, 1 to 25% by weight of the active compound (I), the remainder being a solid carrier.

Wettable powders may conveniently contain, for example, 25 to 90% by weight of the active compound (I), the remainder being a solid carrier and a dispersing and wetting agent, if required, together with a protective colloidal agent, a thixotropic agent, an anti-foaming agent or the like.

Granules may conveniently contain 1 to 35% by weight of the active compound (I), a major portion of the remainder being a solid carrier. The active compound (I) is preferably homogenously mixed with the solid carrier or adhered or adsorbed onto the carrier surface and the size of a granule is suitably about 0.2 to 1.5 mm.

Emulsifiable concentrates may conveniently contain, for example, 5 to 50% by weight of the active compound (I) and about 5 to 20% by weight of an emulsifying agent, the remainder being a liquid carrier, together with a corrosion inhibitor if required.

The herbicidal compositions of this invention, which can be formulated into various types of preparations as described above, may be applied in a paddy or dry field at 10 to 2000 g, preferably 100 to 500 g, of the active ingredient per 10 ares, for pre- or post-emergence soil treatment in order to control weeds effectively. Also, in order to control weeds unselectively in unplanted areas such as roads, grounds, house sites, railways and the like, an application rate of the active ingredient of 200 to 4000 g per ares can be effective.

The herbicidal compositions of this invention may conveniently be blended with other herbicides for broader herbicidal spectra. In some cases, a synergistic effect may be expected, though in general the nature of any other herbicide is not critical. As examples of such other herbicides may be mentioned, for instance,
triazine type herbicides such as
2-methylthio-4,6-bisethylamino-1,3,5-triazine,
2-chloro-4,6-bisethylamino-1,3,5-triazine,
2-methoxy-4-ethylamino-6-isopropylamino-1,3,5-triazine,
2-chloro-4-ethylamino-6-isopropylamino-s-triazine,
2-methylthio-4,6-bis(isopropylamino)-s-triazine,
2-methylthio-4-ethylamino-6-isopropylamino-s-triazine, or
2-methylthio-4-(1,2-dimethylpropylamino)-6-ethylamino-s-triazine;
phenoxy type herbicides such as
2,4-dichlorophenoxyacetic acid or its ethyl, propyl or butyl ester,
4-chloro-2-methylphenoxyacetic acid, or ethyl 2-methyl-4-chlorophenoxybutyrate;
diphenylether type herbicides such as
2,4,6-trichlorophenyl 4'-nitrophenyl ether,
2,4-dichlorophenyl 4'-nitrophenyl ether,
3,5-dimethylphenyl 4'-nitrophenyl ether,
2,4-dichlorophenyl 3'-methoxycarbonyl-4'-nitrophenyl ether, or
2,4-dichlorophenyl 4'-nitro-3'-methoxyphenyl ether;
urea type herbicides such as
3-(3,4-dichlorophenyl)-1-methoxy-1-methylurea,
3-(3,4-dichlorophenyl)-1,1-dimethylurea,
3-(4-chlorophenyl)-1,1-dimethylurea, or
1-($\alpha,\alpha$-dimethylbenzyl)-3-(4-methylphenyl)urea;
carbamate type herbicides such as
3-methoxycarbonylaminophenyl N-(3-methylphenyl)-carbamate,
isopropyl N-(3-chlorophenyl)carbamate, or
methyl N-(3,4-dichlorophenyl)carbamate;
uracil type herbicides such as
5-bromo-3-sec-butyl-6-methyluracil, or
1-cyclohexyl-3,5-propyleneuracil;
thiolcarbamate type herbicides such as
S-(4-chlorobenzyl) N,N-diethylthiolcarbamate,
S-ethyl N-cyclohexyl-N-ethylthiolcarbamate,
S-ethyl hexahydro-1H-azepine-1-carbothioate, or
S-ethyl N,N-di-n-propylthiocarbamate;
pyridinium salt type herbicides such as
1,1'-dimethyl-4,4'bispyridinium dichloride;
phosphorus type herbicides such as
N-(phosphonomethyl)glycine;
aniline type herbicides such as
$\alpha,\alpha,\alpha$-trifluoro-2,6-dinitro-N,N-dipropyl-p-toluidine, or
4-(methylsulphonyl)-2,6-dinitro-N,N-dipropylaniline;
acid anilide type herbicides such as
benzothiazol-2-yloxyacetic acid N-methylanilide,
2-chloro-2',6'-diethyl-N-(butoxymethyl)acetanilide,
2-chloro-2',6'-diethyl-N-(methoxymethyl)acetanilide,
3,4-dichloropropionic anilide, or
2-chloro-2',6'-diethyl-N-(propoxyethyl)acetanilide; or
other herbicides such as
5-tert-butyl-3-(2,4-dichloro-5-isopropoxyphenyl)-1,3,4-oxadiazolin-2-one,
2-[N-isopropyl-N-(4-chlorophenyl)carbamoyl]-4-chloro-5-methyl-4-isoxazolin-3-one,
3-isopropyl-1H-2,1,3-benzothiadiazine-(4)-3H-one 2,2-dioxide,
3-(2-methylphenoxy)pyridazine,
N-(O,O-dipropyldithiophosphorylacetyl)-2-methyl-piperidine,
N-($\alpha,\alpha$-dimethylbenzyl)-$\alpha$-bromo-$\alpha$-tert-butylacetamide,
O,O-diisopropyl S-(2-benzenenesulphonylaminoethyl) phosphorodithioate, or
3,3'-dimethyl-4-methoxybenzophenone.

The herbicides of this invention may also be applied in admixture with other auxiliary materials, including plant growth regulators such as sodium naphthyl acetate, 1,2-dihydropyridazine-3,6-dione, or gibberellins; fungicides such as methyl 1-(butylcarbamoyl)-2-benzimidazolecarbamate, 1,2-bis(3-methoxycarbonyl-2-thioureido)benzene, 3-hydroxy-5-methylisoxazole, N-2,3-dichlorophenyltetrachlorophthalamic acid, 5-methyl-s-triazolo-[3,4-b]benzothiazole, O,O-diisopropyl S-benzyl phosphorothioate, pentachloronitrobenzene, kasugamycin, blasticidin S, or 4,5,6,7-tetrachlorophthalide; insecticides such as O,O-diethyl O-(2-isopropyl-4-methyl-6-pyrimidinyl) phosphorothioate, O,O-diethyl S-2-[(ethylthio)ethyl] phosphorodithioate, 1-naphthyl N-methylcarbamate, O,O-dimethyl O-(3-methyl-4-nitrophenyl) thiophosphate, O,O-dimethyl S-(N-methylcarbamoylmethyl) phosphorodithioate, S-methyl N-[(methylcarbamoyl)oxy]thioacetimidate, O,O-dimethyl S-(N-methyl-N-formylcarbamoyl-methyl) phosphorodithioate, O,O-dimethyl S-2-(ethylthio)ethyl phosporodithioate, O,O-diethyl S-2-[(ethylthio)ethyl] phosphorodithioate, or O,O-dimethyl 1-hydroxy-2,2,2-trichloroethyl phosphonate, or fertilizers.

EXAMPLES OF THE INVENTION

Example 1

5-(2-anilinoethoxy)-4-(2,4-dichlorobenzoyl)-1,3-dimethylpyrazole (Compound 1)

0.08 g of sodium metal was dissolved with heating in 2 ml of 2-anilinoethanol, and then 1 g of 5-chloro-4-(2,4-dichlorobenzoyl)-1,3-dimethylpyrazole was added. The resulting mixture was heated at 100° to 110° C. for 3 hours with stirring. Excess 2-anilinoethanol was distilled off under reduced pressure. The residue was then washed with chloroform and filtered. The chloroform solution was washed with water and dried over anhydrous sodium sulphate. Chloroform was distilled off and the residue was purified by silica gel chromatography (eluent, benzene:acetone at 7:1) to give 0.92 g of the desired product, Compound 1, having a refractive index $n_D^{24}$ 1.6105 (yield 69%).

Example 2

4-(2,4-dichlorobenzoyl)-1,3-dimethyl-5-[2-(N-methylanilino)ethoxy]pyrazole (Compound 2)

A mixture of 1.1 g of 5-(2-bromoethoxy)-4-(2,4-dichlorobenzoyl)-1,3-dimethylpyrazole and 6 ml of N-methylaniline was heated at 110° to 120° C. for 3 hours with stirring. Excess N-methylaniline was distilled off under reduced pressure. The residue was then purified by silica gel chromatography (eluent, benzene:ethyl acetate at 10:1) to give 0.71 g of the desired product, Compound 2, having a refractive index $n_D^{24}$ 1.5975 (yield 60.5%).

The following compounds were prepared following the procedure of Example 2.
4-(2,4-dichlorobenzoyl)-1,3-dimethyl-5-[2-(N,N-diethylamino)ethoxy]pyrazole (Compound 7) $n_D^{24}$ 1.5559
4-(2,4-dichlorobenzoyl)-1,3-dimethyl-5-(3-anilinopropoxy)pyrazole (Compound 8) $n_D^{24}$ 1.5928

Example 3

4-(2,4-dichlorobenzoyl)-1,3-dimethyl-5-[2-(N-methylanilino)ethoxy]pyrazole (Compound 2)

2.85 g of 4-(2,4-dichlorobenzoyl)-1,3-dimethyl-5-hydroxypyrazole was dissolved in 50 ml of acetonitrile, and 1.38 g of potassium carbonate (anydrous) was added thereto. The resultant mixture was stirred at room temperature for 2 hours, 2.14 g of β-bromoethyl-N-methylaniline was added, and the mixture heated for 3 hours under reflux. After cooling, crystals were filtered off. The filtrate was distilled under reduced pressure and the residue was purified by silica gel chromatography (eluent, benzene:ethyl acetate at 8:1) to give 3.82 g of the desired product, Compound 2, having $n_D^{24}$ 1.5975 (yield 91.4%).

Following the procedure described in Example 3 the following compounds were prepared.
4-(2,4-dichloro-3-methylbenzoyl)-1,3-dimethyl-5-[2-(N-methylanilino)ethoxy]pyrazole (Compound 11) mp 92° to 93° C.
4-(2,4-dichlorobenzoyl)-1,3-dimethyl-5-[2-(N-ethylanilino)ethoxy]pyrazole (Compound 12) $n_D^{25}$ 1.5975
4-(2-nitro-4-chlorobenzoyl)-1,3-dimethyl-5-[2-(N-methylanilino)ethoxy]pyrazole (Compound 17) mp 121° to 122° C.
4-(2-nitro-5-methylbenzoyl)-1,3-dimethyl-5-[2-(N-methylanilino)ethoxy]pyrazole (Compound 18) mp 113.5° to 115° C.

Example 4

4-(2,4-dichlorobenzoyl)-1,3-dimethyl-5-[2-(N-methylanilino)ethoxy]pyrazole (Compound 2)

2.7 g of 5-(2-anilinoethoxy)-4-(2,4-dichlorobenzoyl)-1,3-dimethylpyrazole prepared by the procedure of Example 1 or 3 was dissolved in 25 ml of benzene, then 0.7 ml of dimethyl sulphate was added and the mixture heated under reflux for 3 hours with stirring. After cooling of the mixture and washing with water, the organic layer was dried over anhydrous sodium sulphate and the solvent distilled off to give 2.4 g of the desired product, Compound 2, similar to that of Examples 2 and 3 (yield 86%).

Example 5

5-[2-(N-benzylanilino)ethoxy]-4-(2,4-dichlorobenzoyl)-1,3-dimethylpyrazole (Compound 14)

1.01 g of 5-(2-anilinoethoxy)-4-(2,4-dichlorobenzoyl)-1,3-dimethylpyrazole prepared as in Example 1 or 3 was dissolved in a solution of 0.17 g of potassium hydroxide in 8 ml of ethanol and then the mixture was stirred at room temperature for 30 minutes. 2 ml of benzyl bromide was added to the mixture, which was then stirred for a further 5 hours at room temperature, after which the solvent was distilled off under reduced pressure.

Benzene was added, and the mixture washed with water and dried over anhydrous sodium sulphate. After the benzene had been distilled off, the residue was purified by column chromatography through silica gel, eluted with a 10:1 by volume mixture of benzene and ethyl acetate, to give 0.87 g of the desired product, Compound 14, with refractive index $n_D^{33}$ 1.6075, yield 70%.

Following the procedure of Example 5, the following compound was prepared:
5-[2-(N-allylanilino)ethoxy]-4-(2,4-dichlorobenzoyl)-1,3-dimethylpyrazole (Compound 13) $n_D^{27}$ 1.5884

REFERENCE EXAMPLE 5-(2-bromoethoxy)-4-(2,4-dichlorobenzoyl)-1,3-dimethylpyrazole 1.32 g of potassium hydroxide was dissolved in 10 ml of water, and 5.7 g of 4-(2,4-dichlorobenzoyl)-1,3-dimethyl-5-hydroxypyrazole was dissolved in this solution. The water was distilled off under reduced pressure and the residue dried to give the potassium salt. 11.28 g of ethylene dibromide was dissolved in 10 ml of dimethylformamide, and the prepared potassium salt in solution in 30 ml of dimethylformamide was added dropwise over 2 hours with stirring at 110±5° C. After the addition was finished, the reaction mixture was heated for 1.5 hours. The solvent was distilled off under reduced pressure, and the residue was extracted with ethyl acetate. The extract was washed with water and dried over anhydrous sodium sulphate. The solvent was distilled off under reduced pressure and the residue was purified by silica gel chromatography (eluent, benzene:ethyl acetate at 9:1) to give 0.57 g of the desired compound having $n_D^{25}$ 1.5845 (mp 89° to 90° C.) (yield 72.7%).

Following the procedure of this Reference Example, the following compounds were prepared.

5-(3-bromopropoxy)-4-(2,4-dichlorobenzoyl)-1,3-dimethylpyrazole; mp 67° to 68° C.
5-(4-bromobutoxy)-4-(2,4-dichlorobenzoyl)-1,3-dimethylpyrazole; mp 61° C.

These compounds, and generally the compounds (VI), are novel and can be used as herbicides in a similar way to the compounds of formula (I).

EXAMPLE 6

Granules 70 parts of the Compound 2 were finely pulverized and 30 parts of clay were added thereto. The mixture was blended in a mixer to form a premix. 10 Parts of the premix were homogeneously blended in a mixer with 60 parts of clay and 30 parts of bentonite. To the resulting blend was added an appropriate amount of water. The mixture was kneaded in a kneader, extruded through a screen having a diameter of 0.8 mm and dried in a draft drier at 50° C. The obtained product was adjusted by a sifter to give granules.

EXAMPLE 7

Wettable Powder 50 parts of the Compound 7, 29 parts of clay, 10 parts of diatomaceous earth, 5 parts of white carbon, 3 parts of sodium ligninsulphonate, 2 parts of "Newcol" 1106 (Trade name, Nihon Nyukazai KK) and 1 part of polyvinyl alcohol were homogeneously blended in a mixer and pulverized three times by means of a hammermill to give a wettable powder.

EXAMPLE 8

Emulsifiable Concentrate 20 parts of the Compound 1, 65 parts of xylene and 15 parts of "Paracol" PS (Trade name, Nihon Nyukazai) were blended and homogeneously dissolved to form an emulsifiable concentrate.

EXAMPLE 9

Water surface application tests for paddy field weed control

Results were obtained for herbicidal compositions formulated according to the procedure in Example 7 as wettable powders, each containing 50% by weight of the active compound of this invention.

Batches of 3 polyethylene pots (hereinafter abbreviated as A, B and C), each having a surface area of 45 cm², were packed with paddy field soil. In Pot A were transplanted two rice seedlings (variety: Kinmaze) at the 2.5 leaf stage, and two tubers of "Urikawa" as a representative perennial weed. In Pot B, seeds of monochoria, false pimpernel and "Abunome" as representatives of broad-leaved weeds, were incorporated in the soil: Pot B was also planted with a block of runners of slender spike rush and two tubers of "Mizugayatsuri" (flatsedge) as perennial weeds. In Pot C, seeds of barnyard grass and "Hotauri" (*Scripus hotarui Ohwi*), as representative of narrow-leaved weeds, were incorporated in the soil: Pot C was also planted with two tubers of "Omodaka", as a perennial weed.

The Pots A, B and C were then kept for three days in a greenhouse under simulated paddy field conditions. After the plants had rooted, suspensions of the test chemicals were applied into the paddy water at the top of the pots, at the rate of 10 ml per pot. Twenty days after this treatment, the herbicidal effect on the weeds and phytotoxicity to the rice plants were observed and evaluated.

The results are shown in Table 1, wherein the effective dose (grams per are) means the minimum dose for a growth inhibition rate for each tested plant (chlorotic leaf area) of no less than 70%.

TABLE 1

| Compound No | Barnyard grass | Broad-leaved weeds | "Hotarui" | "Urikawa" | Slender spike-rush | "Mizugaya-tsuri" | "Omodaka" | Rice seedling transplanted |
|---|---|---|---|---|---|---|---|---|
| 1 | 6.25 | 6.25 | 12.5 | 25 | 50 | 12.5 | 12.5 | 200 |
| 2 | 6.25 | 6.25 | 12.5 | 12.5 | 25 | 6.25 | 25 | 200 |
| 7 | 12.5 | 25 | 25 | 12.5 | 50 | 25 | 25 | 400 |
| 8 | 12.5 | 6.25 | 6.25 | 25 | 75 | 6.25 | 50 | 400 |
| 11 | 12.5 | 6.25 | 25 | 25 | 50 | 50 | 25 | >400 |
| 12 | 12.5 | 6.25 | 12.5 | 12.5 | 25 | 25 | 25 | 200 |
| 13 | 12.5 | 6.25 | 12.5 | 25 | 50 | 6.25 | 12.5 | 200 |
| 14 | 25 | 6.25 | 12.5 | 25 | 50 | 12.5 | 12.5 | 200 |
| 17 | 25 | 6.25 | 12.5 | 25 | 25 | 6.25 | 25 | 200 |
| 18 | 50 | 6.25 | 50 | 6.25 | 12.5 | 6.25 | 12.5 | 200 |

We claim:

1. A pyrazole derivative having the formula (I):

wherein:
R$^1$ is selected from the group consisting of a methyl group, a halogen atom and a nitro group;
n is 2 or 3;
R$^2$ is selected from the group consisting of a hydrogen atom, an alkyl group having 1 to 4 carbon atoms, an alkenyl group having 3 or 4 carbon atoms, an alkylphenyl group having 1 or 2 carbon atoms in the alkyl portion and an alkylphenyl group having 1 or 2 carbon atoms in the alkyl portion and substituted with a C$_1$-C$_4$ alkyl group in the phenyl portion;
R$^3$ is selected from the group consisting of an alkyl group having 1 to 4 carbon atoms, an alkenyl group having 3 or 4 carbon atoms and a phenyl group; and
A is an alkylene group having from 1 to 5 carbon atoms.

2. A pyrazole derivative according to claim 1, wherein R$^2$ is selected from the group consisting of a hydrogen atom, a methyl group, an ethyl group, an allyl group and a benzyl group, R$^3$ is selected from the group consisting of a methyl group, an ethyl group and a phenyl group, and A is an ethylene group.

3. A pyrazole derivative according to claim 2, wherein n is 2 and the two $R^1$ substituents are chlorine atoms at the 2- and 4-positions of the phenyl ring.

4. A pyrazole derivative according to claim 1, selected from the group consisting of:
5-(2-anilinoethoxy)-4-(2,4-dichlorobenzoyl)-1,3-dimethyl-pyrazole
4-(2,4-dichlorobenzoyl)-1,3-dimethyl-5-[2-(N-methylanilino)ethoxy]pyrazole
4-(2,4-dichlorobenzoyl)-1,3-dimethyl-5-[2-(N,N-diethylamino)ethoxy]pyrazole
4-(2,4-dichlorobenzoyl)-1,3-dimethyl-5-(3-anilinopropoxy)-pyrazole
4-(2,4-dichloro-3-methylbenzoyl)-1,3-dimethyl-5-[2-(N-methylanilino)ethoxy]pyrazole
4-(2,4-dichlorobenzoyl)-1,3-dimethyl-5-[2-(N-ethylanilino)ethoxy]pyrazole
4-(2-nitro-4-chlorobenzoyl)-1,3-dimethyl-5-[2-(N-methyl-anilino)ethoxy]pyrazole
4-(2-nitro-5-methylbenzoyl)-1,3-dimethyl-5-[2-(N-methyl-anilino)ethoxy]pyrazole
5-[2-(N-benzylanilino)ethoxy]-4-(2,4-dichlorobenzoyl)-1,3-dimethylpyrazole
5-[2-(N-allylanilino)ethoxy]-4-(2,4-dichlorobenzoyl)-1,3-dimethylpyrazole.

5. A herbicidal composition containing a carrier or a herbicidally effective amount of a pyrazole derivative having the formula (I):

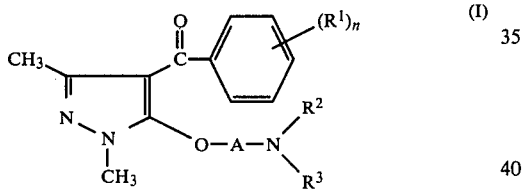

wherein:
$R^1$ is selected from the group consisting of a methyl group, a halogen atom and a nitro group;
n is 2 or 3;
$R^2$ is selected from the group consisting of a hydrogen atom, an alkyl group having 1 to 4 carbon atoms, an alkenyl group having 3 or 4 carbon atoms, an alkylphenyl group having 1 to 2 carbon atoms in the alkyl portion and an alkylphenyl group having 1 or 2 carbon atoms in the alkyl portion and substituted with a $C_1$–$C_4$ alkyl group in the phenyl portion;
$R^3$ is selected from the group consisting of an alkyl group having 1 to 4 carbon atoms, an alkenyl group having 3 or 4 carbon atoms and a phenyl group; and
A is an alkylene group having from 1 to 5 carbon atoms.

6. A method of combatting weeds wherein a herbicidally effective amount of a pyrazole derivative having the formula (I):

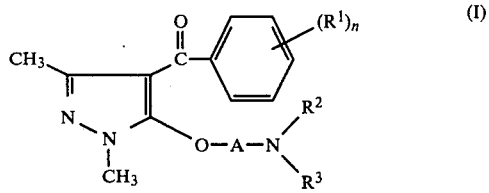

wherein:
$R^1$ is selected from the group consisting of a methyl group, a halogen atom and a nitro group;
n is 2 or 3;
$R^2$ is selected from the group consisting of a hydrogen atom, an alkyl group having 1 to 4 carbon atoms, an alkenyl group having 3 or 4 carbon atoms, an alkylphenyl group having 1 or 2 carbon atoms in the alkyl portion and an alkylphenyl group having 1 or 2 carbon atoms in the alkyl portion and substituted with a $C_1$–$C_4$ alkyl group in the phenyl portion;
$R^3$ is selected from the group consisting of an alkyl group having 1 to 4 carbon atoms, an alkenyl group having 3 to 4 carbon atoms and a phenyl group; and
A is an alkylene group having from 1 to 5 carbon atoms; is applied to the situs of the weeds.

* * * * *

UNITED STATES PATENT AND TRADEMARK OFFICE
CERTIFICATE OF CORRECTION

PATENT NO. : 4,460,597

DATED : July 17, 1984

INVENTOR(S) : Toshiaki YANAI et al

It is certified that error appears in the above-identified patent and that said Letters Patent is hereby corrected as shown below:

Column 15, line 30 (Claim 5, line 1): after "or" insert
--diluent and--.

Signed and Sealed this

Eighteenth Day of June 1985

[SEAL]

Attest:

DONALD J. QUIGG

Attesting Officer

Acting Commissioner of Patents and Trademarks